United States Patent
Chen et al.

(10) Patent No.: US 11,554,354 B2
(45) Date of Patent: Jan. 17, 2023

(54) MICRO-REACTION SYSTEM AND METHOD FOR PREPARING 2-METHYL-4-AMINO-5-AMINOMETHYL PYRIMIDINE

(71) Applicant: Fudan University, Shanghai (CN)

(72) Inventors: Fener Chen, Shanghai (CN); Meifen Jiang, Shanghai (CN); Dang Cheng, Shanghai (CN); Minjie Liu, Shanghai (CN); Huashan Huang, Shanghai (CN)

(73) Assignee: Fudan University, Shanghai (CN)

( * ) Notice: Subject to any disclaimer, the term of this patent is extended or adjusted under 35 U.S.C. 154(b) by 0 days.

(21) Appl. No.: 17/467,041

(22) Filed: Sep. 3, 2021

(65) Prior Publication Data

US 2021/0394148 A1     Dec. 23, 2021

(30) Foreign Application Priority Data

Nov. 8, 2020   (CN) .......................... 202011235050.X

(51) Int. Cl.
| | | |
|---|---|---|
| *B01J 8/00* | (2006.01) |
| *B01J 8/02* | (2006.01) |
| *B01J 8/06* | (2006.01) |
| *B01J 19/00* | (2006.01) |
| *B01J 23/755* | (2006.01) |

(Continued)

(52) U.S. Cl.
CPC .......... *B01J 19/0093* (2013.01); *B01J 25/02* (2013.01); *C07D 239/42* (2013.01);
(Continued)

(58) Field of Classification Search
CPC ......... B01J 8/00; B01J 8/02; B01J 8/06; B01J 8/065; B01J 19/00; B01J 19/0093; B01J 23/00; B01J 23/70; B01J 23/74; B01J 23/755; B01J 25/00; B01J 25/02; B01J 2219/00; B01J 2219/00781; B01J 2219/00889; B01J 2219/00905;
(Continued)

(56) References Cited

U.S. PATENT DOCUMENTS

| | | |
|---|---|---|
| 2,820,050 A | 1/1958 | Hultquist |
| 3,689,498 A | 9/1972 | Leimgruber et al. |

(Continued)

FOREIGN PATENT DOCUMENTS

| | | |
|---|---|---|
| CN | 103261173 A | 8/2013 |
| DE | 2323845 A1 | 11/1973 |

(Continued)

OTHER PUBLICATIONS

Niinobe et al. (DE 2948343 C2), published on Dec. 14, 1988 and provided with a machine translation. (Year: 1988).*

(Continued)

*Primary Examiner* — Natasha E Young

(57) ABSTRACT

A micro-reaction system and a method for preparing 2-methyl-4-amino-5-aminomethyl pyrimidine. A Raney nickel catalyst is modified with formalin, and the modified Raney nickel catalyst is filled into a micro-channel reactor of the micro-reaction system. A substrate solution containing 2-methyl-4-amino-5-cyanopyrimidine and a base and hydrogen are transported to the micro-mixer and the micro-channel reactor in sequence for continuous catalytic hydrogenation to obtain 2-methyl-4-amino-5-aminomethyl pyrimidine.

10 Claims, 1 Drawing Sheet

(51) Int. Cl.
  *B01J 25/02* (2006.01)
  *C07D 239/42* (2006.01)
(52) U.S. Cl.
  CPC ............... *B01J 2219/00889* (2013.01); *B01J 2219/00909* (2013.01); *B01J 2219/00961* (2013.01); *B01J 2219/00963* (2013.01)
(58) Field of Classification Search
  CPC ...... B01J 2219/00909; B01J 2219/0095; B01J 2219/00952; B01J 2219/00954; B01J 2219/00959; B01J 2219/00961; B01J 2219/00963; B01J 2219/00984; C07D 239/00; C07D 239/24; C07D 239/28; C07D 239/32; C07D 239/42
  See application file for complete search history.

(56) References Cited

U.S. PATENT DOCUMENTS

| | | |
|---|---|---|
| 3,792,076 A | 2/1974 | Leimgruber et al. |
| 3,853,946 A | 12/1974 | Leimgruber et al. |
| 3,901,888 A | 8/1975 | Leimgruber et al. |
| 4,794,182 A * | 12/1988 | Takanohashi ........ C07D 239/42 544/329 |
| 2008/0275653 A1* | 11/2008 | Cypes .................... B01D 3/065 210/255 |
| 2019/0151846 A1* | 5/2019 | Kornilovich ...... B01L 3/502761 |

FOREIGN PATENT DOCUMENTS

| | | |
|---|---|---|
| GB | 772256 A | 4/1957 |
| WO | 2012075677 A1 | 6/2012 |

OTHER PUBLICATIONS

Todd artd Bergel.a method for preparing 2-methyl-4-amino-5-aminomethyl pyrimidine through hydrolysis of 2-methyl-4-amino-5-acetamidomethyl pyrimidine.(J. Chem. Soc., 1937, 364).
Fener Chen et al. 2-methyl-4-amino-5-cyanopyrimidine was catalytically hydrogenated to prepare 2-methyl-4-amino-5-aminomethyl pyrimidine.(Org. Process. Res. Dev., 2012, 16, 57).

* cited by examiner

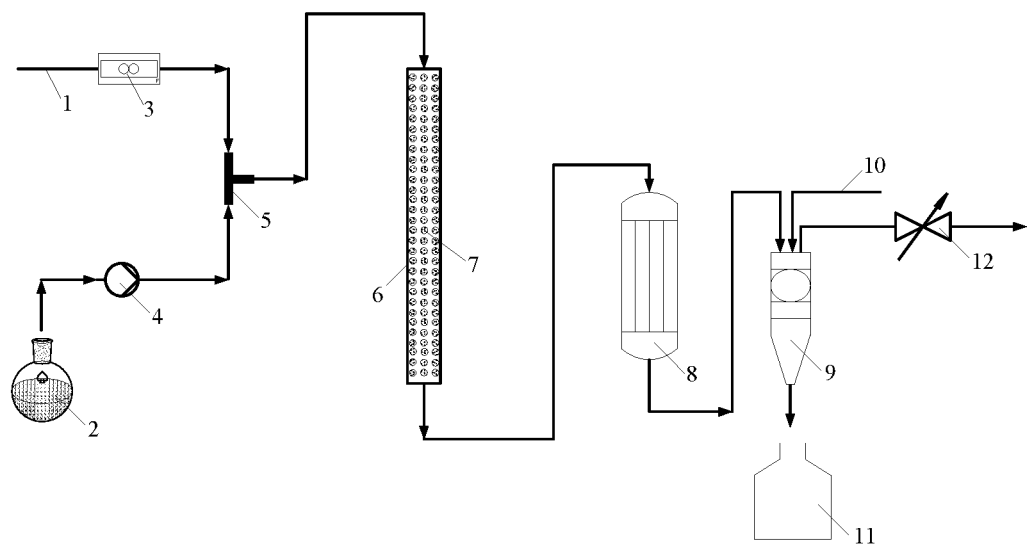

MICRO-REACTION SYSTEM AND METHOD FOR PREPARING 2-METHYL-4-AMINO-5-AMINOMETHYL PYRIMIDINE

CROSS-REFERENCE TO RELATED APPLICATIONS

This application claims the benefit of priority from Chinese Patent Application No. 202011235050. X, filed on Nov. 8, 2020. The content of the aforementioned application, including any intervening amendments thereto, is incorporated herein by reference in its entirety.

TECHNICAL FIELD

This application relates to pharmaceutical engineering, and more particularly to a micro-reaction system and a method for preparing 2-methyl-4-amino-5-aminomethyl pyrimidine.

BACKGROUND 2-methyl-4-amino-5-aminomethyl pyrimidine of formula (I) is a key intermediate for the synthesis of vitamin $B_1$.

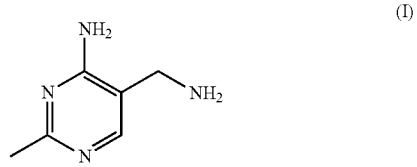

U.S. Pat. Nos. 3,689,498, 3,792,076, 3,853,946, 3,901,888 and 2,820,050, GB Patent No. 772256, DE Patent No. 2323845, and Todd and Bergel. (*J. Chem. Soc.,* 1937, 364) all disclosed a method for preparing 2-methyl-4-amino-5-aminomethyl pyrimidine through hydrolysis of 2-methyl-4-amino-5-acetamidomethyl pyrimidine. However, this method had long synthetic route, complex process, high cost and serious environmental pollution, and thus is not suitable for the industrial application.

Another preparation strategy has been reported by World Patent No. 2012/075677, Chinese Patent No. 103261173 and Fener Chen et al. (*Org. Process. Res. Dev.,* 2012, 16, 57), in which 2-methyl-4-amino-5-cyanopyrimidine was catalytically hydrogenated to prepare 2-methyl-4-amino-5-aminomethyl pyrimidine. Specifically, readily-available cyanoacetamide was used as a starting material and dehydrated in-situ to form malononitrile, which was then reacted with a Vilsmeier reagent to obtain (dimethylaminomethylene)malononitrile. Finally, the resultant (dimethylaminomethylene) malononitrile and acetamidine hydrochloride were subjected to condensation to obtain 2-methyl-4-amino-5-cyanopyrimidine. This method allowed for shortened synthesis route and reduced cost of raw materials, but it still struggled with long reaction time, high reaction pressure, high risk, large energy consumption and low efficiency. Moreover, the above methods all are carried out in traditional batch reactors, failing to accomplish the continuous preparation of 2-methyl-4-amino-5-aminomethyl pyrimidine. Therefore, there is an urgent need for those skilled in the art to develop a rapid, energy-saving, efficient and intrinsically-safe method for continuously preparing 2-methyl-4-amino-5-aminomethyl pyrimidine.

SUMMARY

An object of this application is to provide a method for preparing 2-methyl-4-amino-5-aminomethyl pyrimidine using a micro-reaction system to overcome the defects in the prior art. The method provided herein has shortened reaction time, significantly improved degree of automation and efficiency, greatly reduced energy consumption, greatly enhanced safety, and thus is suitable for industrial production.

The technical solutions of this application are specifically described as follows.

In a first aspect, this application provides a method for preparing 2-methyl-4-amino-5-aminomethyl pyrimidine using a micro-reaction system, wherein the micro-reaction system comprises a micro-mixer and a micro-channel reactor communicated in sequence; and the method comprises:

(1) modifying a Raney nickel catalyst with formalin to obtain a modified Raney nickel catalyst; and filling the micro-channel reactor with the modified Raney nickel catalyst;

(2) transporting a substrate solution containing 2-methyl-4-amino-5-cyanopyrimidine and a base and hydrogen gas to the micro-mixer followed by mixing; allowing the reaction mixture flowing out of the micro-mixer to enter into the micro-channel reactor; and subjecting the reaction mixture to catalytic hydrogenation; and (3) collecting the reaction mixture flowing out of the micro-reaction system; and subjecting the reaction mixture to separation and purification to obtain a target product 2-methyl-4-amino-5-aminomethyl pyrimidine;

wherein the 2-methyl-4-amino-5-aminomethyl pyrimidine is shown in formula (I), and the 2-methyl-4-amino-5-cyanopyrimidine is shown in formula (II); and the catalytic hydrogenation is shown in the following reaction scheme:

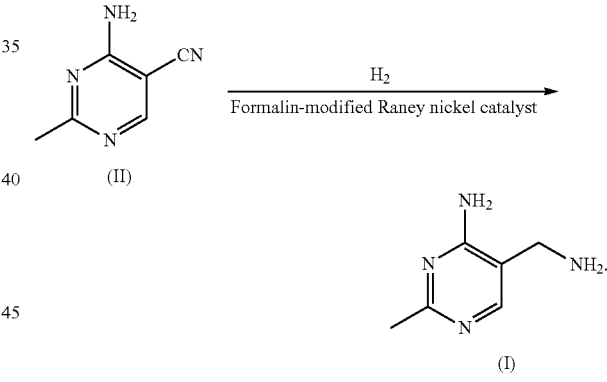

In some embodiments, the step (1) comprises:

(a) dispersing the Raney nickel catalyst in a liquid dispersion medium; adding a formalin solution, where the formalin solution is 0.5-30% by weight of the Raney nickel catalyst; and stirring the reaction mixture at 10-75° C. for 10 min-3 h in an inert gas; and (b) filtering the reaction mixture to collect a filter residue; washing the filter residue with deionized water several times to obtain the modified Raney nickel catalyst; and storing the modified Raney nickel catalyst in water.

In some embodiments, a particle size of the Raney nickel catalyst is equal to or larger than 20 mesh, preferably 40-60 mesh.

In some embodiments, a weight ratio of the Raney nickel catalyst to the liquid dispersion medium is (0.1-0.65):1, preferably (0.25-0.60):1.

In some embodiments, the liquid dispersion medium is water, an organic solvent or a mixture thereof.

In some embodiments, the organic solvent is a $C_1$-$C_4$ alkanol selected from the group consisting of methanol, ethanol, ethylene glycol, 1-propanol, 2-propanol, 1,2-propanediol, 1,3-propanediol, 1-butanol and a combination thereof.

In some embodiments, the liquid dispersion medium is a mixture of water and one organic solvent, such as a mixture of water and methanol and a mixture of water and ethanol, or a mixture of two or more organic solvents, such as a mixture of ethanol and ethylene glycol.

In some embodiments, the inert gas is selected from the group consisting of nitrogen, argon, helium and neon.

In some embodiments, in step (a), the stirring is performed at 15-50° C.

In some embodiments, in step (2), the substrate solution is prepared by dissolving 2-methyl-4-amino-5-cyanopyrimidine and the base in methanol.

In an embodiment, the base is an inorganic base or an organic base; where the inorganic base is ammonia water or hydrazine hydrate, and the organic base is selected from the group consisting of methylamine, urea, ethylamine, ethanolamine, ethylenediamine, dimethylamine, trimethylamine, triethylamine, propylamine, isopropylamine, 1,3-propanediamine, 1,2-propanediamine, tripropylamine, triethanolamine, butylamine, isobutylamine, tert-butylamine, tributylamine, hexylamine, octylamine, aniline, benzylamine, cyclohexylamine and pyridine.

In some embodiments, in the substrate solution, a molar ratio of 2-methyl-4-amino-5-cyanopyrimidine to the base is 1:(1-10), preferably 1:(3-8).

In some embodiments, in step (2), flow rates of the substrate solution and hydrogen gas are adjusted such that a molar ratio of 2-methyl-4-amino-5-cyanopyrimidine to hydrogen gas in the micro-mixer is 1:(0.95-1.4);

a temperature in the micro-mixer is controlled to 5-120° C.;

a temperature in the micro-channel reactor is controlled to 20-150° C.; and a residence time of the reaction mixture in the micro-channel reactor is 0.1-15 min.

In some embodiments, the micro-mixer is a static mixer, a T-type micro-mixer, a Y-type micro-mixer, a coaxial flow micro-mixer or a flow-focusing micro-mixer.

In some embodiments, the micro-channel reactor is a tubular micro-channel reactor or a plate-type micro-channel reactor.

In some embodiments, an inner diameter of the tubular micro-channel reactor is 100 μm-50 mm, preferably 120 μm-30 mm.

In some embodiments, a hydraulic diameter of a reaction fluid channel of the plate-type micro-channel reactor is 100 μm-50 mm, preferably 120 μm-30 mm.

In some embodiments, the micro-reaction system further comprises a feed pump, a gas mass flow meter equipped with a flow controller, a condenser, a gas-liquid separator and a back pressure valve; one inlet of the micro-mixer is connected to the gas mass flow meter, and the other inlet of the micro-mixer is connected to the feed pump; an outlet of the micro-mixer is connected to an inlet of the micro-channel reactor, and an outlet of the micro-channel reactor is connected to an inlet of the condenser; a top of the gas-liquid separator is provided with a first port, a second port and a third port; an outlet of the condenser is connected to the first port; the second port is configured to introduce nitrogen to provide a pressure in the gas-liquid separator; a pressure of the nitrogen is 0.1-4.5 MPa; the third port is connected to the back pressure valve; a back pressure of the back pressure valve is 0.1-4 MPa; and a pressure of the nitrogen is 0.2-0.5 MPa larger than a back pressure value set by the back pressure valve.

In some embodiments, the step (3) comprises:
collecting the reaction mixture flowing out of the micro-reaction system; and subjecting the reaction mixture to concentration under vacuum and drying to obtain the target product 2-methyl-4-amino-5-aminomethyl pyrimidine.

In a second aspect, this application provides a micro-reaction system for preparing 2-methyl-4-amino-5-aminomethyl pyrimidine, comprising:
a feed pump;
a gas mass flow meter equipped with a flow controller;
a micro-mixer;
a micro-channel reactor;
a condenser;
a gas-liquid separator; and
a back pressure valve;

wherein the micro-mixer is provided with two inlets; one inlet of the micro-mixer is connected to the gas mass flow meter, and the other inlet of the micro-mixer is connected to the feed pump; an outlet of the micro-mixer is connected to an inlet of the micro-channel reactor, and an outlet of the micro-channel reactor is connected to an inlet of the condenser; a top of the gas-liquid separator is provided with a first port, a second port and a third port; an outlet of the condenser is connected to the first port; the second port is configured introduce nitrogen to provide a pressure in the gas-liquid separator; a pressure of the nitrogen is 0.1-4.5 MPa; the back pressure valve is connected to the third port, and a back pressure of the back pressure valve is 0.1-4 MPa; and a pressure of the nitrogen is 0.2-0.5 MPa larger than a back pressure value set by the back pressure valve;

the micro-channel reactor is filled with a formalin-modified Raney nickel catalyst;

the feed pump and the gas mass flow meter are configured to transport a substrate solution containing 2-methyl-4-amino-5-cyanopyrimidine and hydrogen to the micro-mixer, respectively; the micro-mixer is configured for mixing the substrate solution with hydrogen obtain a reaction mixture; the reaction mixture flowing out of the micro-mixer enters into the micro-channel reactor and undergoes a catalytic hydrogenation; after flowing out of the micro-channel reactor, the reaction mixture is cooled in the condenser, and then enters the gas-liquid separator; a waste gas generated in the gas-liquid separator is discharged through the third port and the back pressure valve; and the reaction mixture is discharged through an outlet provided at a bottom of the gas-liquid separator, collected and subjected to separation and purification to obtain a target product 2-methyl-4-amino-5-aminomethyl pyrimidine;

wherein the 2-methyl-4-amino-5-aminomethyl pyrimidine is shown in formula (I):

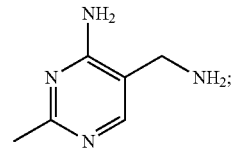

and
the 2-methyl-4-amino-5-cyanopyrimidine is shown in formula (II):

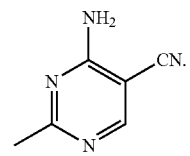

In some embodiments, the micro-channel reactor is a tubular micro-channel reactor or a plate-type micro-channel reactor.

Compared to the preparation methods carried out in a traditional batch reactor, the method provided herein for preparing 2-methyl-4-amino-5-aminomethyl pyrimidine using a micro-reaction system including a micro-mixer and a micro-channel reactor communicated in sequence has the following beneficial effects:

1. This method enables continuous synthesis of 2-methyl-4-amino-5-aminomethyl pyrimidine without external intervention, and has advantages of high degree of automation and excellent space-time efficiency, which significantly reduce the labor intensity and production cost.

2. The catalytic hydrogenation of 2-methyl-4-amino-5-cyanopyrimidine is completed in the reaction fluid channel of the micro-channel reactor, which has a relatively small total volume, so the method of the disclosure has a small online liquid holdup and an intrinsically safe process.

3. The micro-channel reactor possess excellent mass transfer and mixing performances, which enables that the time of the catalytic hydrogenation is shortened from several hours (in the traditional batch reactor) to a few minutes.

4. It is not required to separate the catalyst from the reaction solution due to the continuous flow process of the micro-channel reactor, and thus the reaction system can be operated continuously for a long time, which not only greatly improves the process and space-time efficiency and the yield (>99%), but also significantly reduces the time consumption, cost and labor intensity. By comparison, it is necessary to separate the catalyst from the reaction mixture after the reaction is completed in the batch reactor, and the process of recovering and feeding the catalyst is required to be performed repeatedly, complicating the preparation process.

5. The multiphase mixing, mass transfer and reaction process are completed in the micro-mixer and the reaction fluid channel of the micro-channel reactor in the absence of a stirring device, which greatly reduces the energy consumption.

BRIEF DESCRIPTION OF THE DRAWINGS

The FIGURE schematically shows a structure of a micro-reaction system according to an embodiment of this disclosure.

In the drawing: 1, hydrogen pipeline; 2, storage tank; 3, gas mass flow meter; 4, feed pump; 5, micro-mixer; 6, micro-channel reactor; 7, catalyst; 8, condenser; 9, gas-liquid separator; 10, nitrogen pipeline; 11, collection tank; and 12, back pressure valve.

DETAILED DESCRIPTION OF EMBODIMENTS

The technical solutions, structural features, objects and advantages of the disclosure will be described in detail with reference to the embodiments.

The structure of the micro-reaction system used in the following examples is shown in the FIGURE, which includes a hydrogen pipeline 1, a storage tank 2, a gas mass flow meter 3, a feed pump 4, a micro-mixer 5, a micro-channel reactor 6, a catalyst 7, a condenser 8, a gas-liquid separator 9, a nitrogen pipeline 10, a collection tank 11 and a back pressure valve 12.

One inlet of the micro-mixer 5 is connected to the gas mass flow meter 3, and the other inlet of the micro-mixer 5 is connected to the feed pump 4. An outlet of the micro-mixer 5 is connected to an inlet of the micro-channel reactor 6, and an outlet of the micro-channel reactor 6 is connected to an inlet of the condenser 8. A top of the gas-liquid separator 9 is provided with a first port, a second port and a third port. An outlet of the condenser 8 is connected to the first port. The second port is connected to the nitrogen pipe 10 to introduce nitrogen. The third port is connected to the back pressure valve 12.

The preparation of 2-methyl-4-amino-5-aminomethyl pyrimidine using the micro-reaction system is specifically described as follows.

(a) A formalin-modified Raney nickel catalyst is filled into the micro-channel reactor 6. A substrate solution containing 2-methyl-4-amino-5-cyanopyrimidine and a base is prepared and stored in the storage tank 2.

(b) The substrate solution and hydrogen gas are transported into the micro-mixer 5 simultaneously through the feed pump 4 and the gas mass flow meter 3, respectively. The substrate solution and hydrogen gas are thoroughly mixed in the micro-mixer 5, and the resultant reaction mixture subsequently enters the micro-channel reactor 6 and undergoes a continuous catalytic hydrogenation. After flowing out of the micro-channel reactor 6, the reaction mixture is cooled in the condenser 8 and then enters the gas-liquid separator 9. The waste gas generated in the gas-liquid separator 9 is discharged through the third port on the top of the gas-liquid separator 9 and the back pressure valve 12, and the reaction mixture is discharged through a bottom outlet of the gas-liquid separator 9, collected and subjected to separation and purification to obtain the target product 2-methyl-4-amino-5-aminomethyl pyrimidine.

Example 1

1. Preparation of Modified Raney Nickel Catalyst 40 g of Raney nickel with a particle size of 20-40 mesh was dispersed in 100 g of water, to which a formalin solution was added, where the formalin solution was 5% by weight of the Raney nickel. The reaction mixture was stirred at 25° C. for 2 h under the protection of nitrogen and filtered to collect a filter residue. The filter residue was washed three times with deionized water to produce the modified Raney nickel catalyst, which was stored in water for use.

2. Catalytic Hydrogenation

The modified Raney nickel catalyst prepared herein was filled into a tubular micro-channel reactor with a length of 20 cm and an inner diameter of 1 cm. 5 g of a 25% (by weight) ammonia water was mixed into 200 mL of methanol, to which 2 g (0.015 mol) of 2-methyl-4-amino-5-cyanopyrimidine was added to obtain a substrate solution. The substrate solution and hydrogen were transported to a T-type micro-mixer simultaneously, where a temperature in the T-type micro-mixer was controlled to 70° C.; and flow rates of the substrate solution and hydrogen were adjusted such that a molar ratio of 2-methyl-4-amino-5-cyanopyrimidine to hydrogen in the micro-mixer was 1:1.1. The substrate solution and hydrogen were mixed in the T-type micro-mixer and then directly entered the tubular micro-channel reactor, where the micro-channel reactor filled with modified Raney nickel catalyst had a reaction volume of about 2 mL. A back pressure of the back pressure valve 12 was set to 1.6 MPa, and a pressure of the nitrogen introduced to the gas-liquid separator 9 was adjusted to 1.9 MPa. After reacted in the micro-channel reactor 6 at 100° C. for about 2 min, the reaction mixture flowed out through an outlet of the micro-channel reactor 6, and was condensed by the condenser 8. Then the reaction mixture was subjected to gas-liquid separation by the gas-liquid separator 9 to remove waste gas, and collected into the collection tank 11. Finally, the reaction mixture was subjected to concentration and drying to obtain an off-white solid. The analysis results demonstrated that the substrate 2-methyl-4-amino-5-cyanopyrimidine experienced a complete conversion, and the target product 2-methyl-4-amino-5-aminomethyl pyrimidine had a yield of 100% and a purity greater than 99%.

Example 2

The process in this example was basically the same as that of Example 1 except that in this example, the particle size of Raney nickel used in the modification process was 60-80 mesh. In this example, the substrate 2-methyl-4-amino-5-cyanopyrimidine experienced a 100% conversion, and the target product 2-methyl-4-amino-5-aminomethyl pyrimidine had a yield of 100% and a purity greater than 99%.

Example 3

The process in this example was basically the same as that of Example 2 except that in this example, the catalytic hydrogenation of the substrate solution was performed for about 1.2 min. In this example, the substrate 2-methyl-4-amino-5-cyanopyrimidine experienced a 100% conversion, and the target product 2-methyl-4-amino-5-aminomethyl pyrimidine had a yield of 100% and a purity greater than 99%.

Example 4

The process in this example was basically the same as that of Example 1 except that in this example, the modification of the Raney nickel was performed at 45° C. In this example, the substrate 2-methyl-4-amino-5-cyanopyrimidine experienced a 100% conversion, and the target product 2-methyl-4-amino-5-aminomethyl pyrimidine had a yield of 100% and a purity greater than 99%.

Example 5

The process in this example was basically the same as that of Example 4 except that in this example, the catalytic hydrogenation of the substrate solution was performed for about 5 min. In this example, the substrate 2-methyl-4-amino-5-cyanopyrimidine experienced a 100% conversion, and the target product 2-methyl-4-amino-5-aminomethyl pyrimidine had a yield of 100% and a purity greater than 99%.

Example 6

The process in this example was basically the same as that of Example 1 except that in this example, the Raney nickel catalyst was 10% by weight of the formalin solution in the modification. In this example, the substrate 2-methyl-4-amino-5-cyanopyrimidine experienced a 100% conversion, and the target product 2-methyl-4-amino-5-aminomethyl pyrimidine had a yield of 100% and a purity greater than 99%.

Example 7

The process in this example was basically the same as that of Example 6 except that in this example, the catalytic hydrogenation of the substrate solution was performed for about 1.0 min. In this example, the substrate 2-methyl-4-amino-5-cyanopyrimidine experienced a 100% conversion, and the target product 2-methyl-4-amino-5-aminomethyl pyrimidine had a yield of 100% and a purity greater than 99%.

Example 8

The process in this example was basically the same as that of Example 1 except that in this example, the micro-mixer 5 is a Y-type micro-mixer in the catalytic hydrogenation. In this example, the substrate 2-methyl-4-amino-5-cyanopyrimidine experienced a 100% conversion, and the target product 2-methyl-4-amino-5-aminomethyl pyrimidine had a yield of 100% and a purity greater than 99%.

Example 9

The process in this example was basically the same as that of Example 1 except that in this example, the micro-mixer 5 is a coaxial flow micro-mixer in the catalytic hydrogenation. In this example, the substrate 2-methyl-4-amino-5-cyanopyrimidine experienced a 100% conversion, and the target product 2-methyl-4-amino-5-aminomethyl pyrimidine had a yield of 100% and a purity greater than 99%.

Example 10

The process in this example was basically the same as that of Example 1 except that in this example, the micro-mixer 5 is a flow focusing micro-mixer in the catalytic hydrogenation. In this example, the substrate 2-methyl-4-amino-5-cyanopyrimidine experienced a 100% conversion, and the target product 2-methyl-4-amino-5-aminomethyl pyrimidine had a yield of 100% and a purity greater than 99%.

Example 11

The process in this example was basically the same as that of Example 1 except that in this example, the temperature in the micro-mixer was 100° C. In this example, the substrate 2-methyl-4-amino-5-cyanopyrimidine experienced a 100% conversion, and the target product 2-methyl-4-amino-5-aminomethyl pyrimidine had a yield of 100% and a purity greater than 99%.

Example 12

The process in this example was basically the same as that of Example 1 except that in this example, the temperature in the microchannel reactor was 120° C. In this example, the substrate 2-methyl-4-amino-5-cyanopyrimidine experienced a 100% conversion, and the target product 2-methyl-4-amino-5-aminomethyl pyrimidine had a yield of 100% and a purity greater than 99%.

Example 13

The process in this example was basically the same as that of Example 12 except that in this example, the catalytic hydrogenation of the substrate solution was performed for about 1.3 min. In this example, the substrate 2-methyl-4-amino-5-cyanopyrimidine experienced a 100% conversion, and the target product 2-methyl-4-amino-5-aminomethyl pyrimidine had a yield of 100% and a purity greater than 99%.

Example 14

The process in this example was basically the same as that of Example 1 except that in this example, the temperature in the micro-channel reactor 6 was 70° C. In this example, the substrate 2-methyl-4-amino-5-cyanopyrimidine experienced a 86% conversion, and the target product 2-methyl-4-amino-5-aminomethyl pyrimidine had a yield of 86% and a purity greater than 86%.

Example 15

The process in this example was basically the same as that of Example 1 except that in this example, the inner diameter of the micro-channel reactor 6 was 5 mm. In this example, the substrate 2-methyl-4-amino-5-cyanopyrimidine experienced a 100% conversion, and the target product 2-methyl-4-amino-5-aminomethyl pyrimidine had a yield of 100% and a purity greater than 99%.

Example 16

The process in this example was basically the same as that of Example 15 except that in this example, the catalytic hydrogenation of the substrate solution was performed for about 1.5 min. In this example, the substrate 2-methyl-4-amino-5-cyanopyrimidine experienced a 100% conversion, and the target product 2-methyl-4-amino-5-aminomethyl pyrimidine had a yield of 100% and a purity greater than 99%.

Example 17

The process in this example was basically the same as that of Example 1 except that in this example, the back pressure of the back pressure valve 12 was set to 1.0 MPa and the pressure of the nitrogen introduced to the gas-liquid separator was adjusted to 1.3 MPa. In this example, the substrate 2-methyl-4-amino-5-cyanopyrimidine experienced a 92% conversion, and the target product 2-methyl-4-amino-5-aminomethyl pyrimidine had a yield of 92% and a purity greater than 92%.

Example 18

The process in this example was basically the same as that of Example 17 except that in this example, the catalytic hydrogenation of the substrate solution was performed for about 10 min. In this example, the substrate 2-methyl-4-amino-5-cyanopyrimidine experienced a complete conversion, and the target product 2-methyl-4-amino-5-aminomethyl pyrimidine had a yield of 100% and a purity greater than 99%.

Example 19

1. Preparation of Modified Raney Nickel Catalyst 40 g of Raney nickel with a particle size of 20-40 mesh was dispersed in 100 g of water, to which a formalin solution was added, where the formalin solution was 5% by weight of the Raney nickel. The reaction mixture was stirred at 25° C. for 0.5 h under the protection of nitrogen and filtered to collect a filter residue. The filter residue was washed three times with deionized water to produce the modified Raney nickel catalyst, which was stored in water for use.

2. Catalytic Hydrogenation

The modified Raney nickel catalyst prepared herein was filled into a tubular micro-channel reactor with a length of 20 cm and an inner diameter of 1 cm. 7.44 g of triethylamine (0.0735 mol) was mixed into 200 mL of methanol, to which 2 g (0.015 mol) of 2-methyl-4-amino-5-cyanopyrimidine was added to obtain a substrate solution. The substrate solution and hydrogen were transported to a T-type micro-mixer simultaneously, where a temperature in the T-type micro-mixer was controlled to 110° C., and flow rates of the substrate solution and hydrogen were adjusted such that a molar ratio of 2-methyl-4-amino-5-cyanopyrimidine to hydrogen in the micro-mixer was 1:1.1. The substrate solution and hydrogen were mixed in the T-type micro-mixer and then directly entered the tubular micro-channel reactor 6, where the micro-channel reactor 6 filled with modified Raney nickel catalyst had a reaction volume of about 2 mL. A back pressure of the back pressure valve 12 was set to 2 MPa, and a pressure of the nitrogen introduced to the gas-liquid separator 9 was adjusted to 2.3 MPa. After reacted in the micro-channel reactor 6 at 110° C. for about 2 min, the reaction mixture flowed out through an outlet of the micro-channel reactor 6, and was condensed by the condenser 8. Then the reaction mixture was subjected to gas-liquid separation by the gas-liquid separator 9 to remove waste gas, and collected into the collection tank 11. Finally, the reaction mixture was subjected to concentration and drying to obtain an off-white solid. The analysis results demonstrated that the substrate 2-methyl-4-amino-5-cyanopyrimidine experienced a complete conversion, and the target product 2-methyl-4-amino-5-aminomethyl pyrimidine had a yield of 100% and a purity greater than 99%.

Example 20

1. Preparation of Modified Raney Nickel Catalyst 40 g of Raney nickel with a particle size of 40-60 mesh was dispersed in 100 g of water, to which a formalin solution was added, where the formalin solution was 5% by weight of the Raney nickel. The reaction mixture was stirred at 25° C. for 0.5 h under the protection of nitrogen and filtered to collect a filter residue. The filter residue was washed three times with deionized water to produce the modified Raney nickel catalyst, which was stored in water for use.

2. Catalytic Hydrogenation

The modified Raney nickel catalyst prepared herein was filled into a tubular micro-channel reactor with a length of 20 cm and an inner diameter of 1 cm. 4.34 g of trimethylamine (0.0735 mol) was nixed into 200 mL of methanol to which 2 g (0.015 mol) of 2-methyl-4-amino-5-cyanopyrimidine was added to obtain a substrate solution. The substrate solution and hydrogen were transported to a T-type micro-mixer simultaneously, where a temperature in the T-type micro-mixer was controlled to 70° C., and flow rates of the substrate solution and hydrogen were adjusted such that a molar ratio of 2-methyl-4-amino-5-cyanopyrimidine to hydrogen in the micro-mixer was 1:1.1. The substrate solution and hydrogen were mixed in the T-type micro-mixer and then directly entered the tubular micro-channel reactor, where the micro-channel reactor 6 filled with modified Raney nickel catalyst had a reaction volume of about 2 mL. A back pressure of the back pressure valve 12 was set to 3 MPa, and a pressure of the nitrogen introduced to the gas-liquid separator was adjusted to 3.5 MPa. After reacted in the micro-channel reactor 6 at 100° C. for about 2 min, the reaction mixture flowed out through an outlet of the micro-channel reactor 6, and was condensed by the condenser 8.

Then the reaction mixture was subjected to gas-liquid separation by gas-liquid separator 9 to remove waste gas, and collected into collection tank 11. Finally, the reaction mixture was subjected to concentration and drying to obtain an off-white solid. The analysis results demonstrated that the substrate 2-methyl-4-amino-5-cyanopyrimidine experienced a complete conversion, and the target product 2-methyl-4-amino-5-aminomethyl pyrimidine had a yield of 100% and a purity greater than 99%.

Example 21

1. Preparation of Modified Raney Nickel Catalyst 40 g of Raney nickel with a particle size of 20-40 mesh was dispersed in 100 g of water, to which a formalin solution was added, where the formalin solution was 5% by weight of the Raney nickel. The reaction mixture was stirred at 25° C. for 2 h under the protection of nitrogen and filtered to collect a filter residue. The filter residue was washed three times with deionized water to produce the modified Raney nickel catalyst, which was stored in water for use.

2. Catalytic Hydrogenation

The modified Raney nickel catalyst prepared herein was filled into a tubular micro-channel reactor with a length of 20 cm and an inner diameter of 1 cm. 9.5 g of tributylamine (0.0735 mol) was mixed into 200 mL of methanol, to which 2 g (0.015 mol) of 2-methyl-4-amino-5-cyanopyrimidine was added to obtain a substrate solution. The substrate solution and hydrogen were transported to a T-type micro-mixer simultaneously, where a temperature in the T-type micro-mixer was controlled to 100° C., and flow rates of the substrate solution and hydrogen were adjusted such that a molar ratio of 2-methyl-4-amino-5-cyanopyrimidine to hydrogen in the micro-mixer was 1:1.1. The substrate solution and hydrogen were mixed in the T-type micro-mixer and then directly entered the tubular micro-channel reactor, where the micro-channel reactor 6 filled with modified Raney nickel catalyst had a reaction volume of about 2 mL. A back pressure of the back pressure valve 12 was set to 1.6 MPa, and a pressure of the nitrogen introduced to the gas-liquid separator 9 was adjusted to 1.9 MPa. After reacted in the micro-channel reactor 6 at 100° C. for about 2 min, the reaction mixture flowed out through an outlet of the micro-channel reactor 6, and was condensed by the condenser 8. Then the reaction mixture was subjected to gas-liquid separation by gas-liquid separator 9 to remove waste gas, and collected into collection tank 11. Finally, the reaction mixture was subjected to concentration and drying to obtain an off-white solid. The analysis results demonstrated that the substrate 2-methyl-4-amino-5-cyanopyrimidine experienced a complete conversion, and the target product 2-methyl-4-amino-5-aminomethyl pyrimidine had a yield of 100% and a purity greater than 99%.

Example 22

1. Preparation of Modified Raney Nickel Catalyst 40 g of Raney nickel with a particle size of 20-40 mesh was dispersed in 100 g of water, to which a formalin solution was added, where the formalin solution was 7% by weight of the Raney nickel. The reaction mixture was stirred at 25° C. for 2 h under the protection of nitrogen and filtered to collect a filter residue. The filter residue was washed three times with deionized water to produce the modified Raney nickel catalyst, which was stored in water for use.

2. Catalytic Hydrogenation

The modified Raney nickel catalyst prepared herein was filled into a reaction fluid channel of a plate-type micro-channel reactor made of 316L stainless steel, where the reaction fluid channel had a cross section of 400 μm (width)×600 μm (length), a hydraulic diameter of 480 μm, and a length of 100 mm. The plate-type micro-channel reactor had a cuboid structure with a length of 12 cm, a width of 10 cm and a height of 3 cm, and included a first temperature-control medium layer, a reaction layer and a second temperature-control medium layer from top to bottom. The first temperature-control medium layer and the second temperature-control medium layer were used to adjust and control the temperature of the reaction layer, and the reaction fluid channel was arranged in the reaction layer.

5 g of ammonia water (25% by weight) was mixed into 200 mL of methanol, to which 2 g (0.015 mol) of 2-methyl-4-amino-5-cyanopyrimidine was added to obtain a substrate solution. The substrate solution and hydrogen were transported to a T-type micro-mixer simultaneously, where a temperature in the T-type micro-mixer was controlled to 70° C.; and flow rates of the substrate solution and hydrogen were adjusted such that a molar ratio of 2-methyl-4-amino-5-cyanopyrimidine to hydrogen in the micro-mixer 5 was 1:1.1. The substrate liquid and hydrogen were mixed by the T-type micro-mixer and then directly entered the plate-type micro-channel reactor. A back pressure value of the back pressure valve 12 was set to 1.6 MPa, and a pressure of nitrogen introduced to the gas-liquid separator 9 was adjusted to 1.9 MPa. After reacted at 100° C. for about 2 min, the reaction mixture flowed out from an outlet of the micro-channel reactor 6, and was condensed by the condenser 8 and subjected to gas-liquid separation in the gas-liquid separator 9 to remove waste gas. Finally, the reaction mixture was collected into the collection tank 11 and subjected to concentration and drying to obtain an off-white solid. The analysis results demonstrated that conversion rate of the substrate 2-methyl-4-amino-5-cyanopyrimidine experienced a 100% conversion, and the target product 2-methyl-4-amino-5-aminomethyl pyrimidine had a yield of 100% and a purity greater than 99%.

Example 23

The process in this example was basically the same as that of Example 1 except that in this example, 65 g of Raney nickel with a particle size of 20-40 mesh was dispersed in 100 μg of water. In this example, the substrate 2-methyl-4-amino-5-cyanopyrimidine had a conversion rate of 98%, and the target product 2-methyl-4-amino-5-aminomethyl pyrimidine had a yield of 98% and a purity of 98%.

Example 24

The process provided herein was basically the same as that of Example 1 except that in this example, 1.02 g of ammonia water (25% by weight) was mixed into 200 mL of methanol and then 2 g (0.015 mol) of 2-methyl-4-amino-5-cyanopyrimidine was added to obtain a substrate solution. In this example, the substrate 2-methyl-4-amino-5-cyanopyrimidine had a conversion rate of 95%, and the target product 2-methyl-4-amino-5-aminomethyl pyrimidine had a yield of 95% and a purity of 95%.

Example 25

The process in this example was basically the same as that of Example 1 except that in this example, 10.2 g of ammonia (25% by weight) was mixed into 200 mL of methanol, to which 2 g (0.015 mol) of 2-methyl-4-amino-5-cyanopyrimidine was added to obtain a substrate solution. In this example, the substrate 2-methyl-4-amino-5-cyanopyrimidine had a conversion rate of 97%, and the target product 2-methyl-4-amino-5-aminomethyl pyrimidine had a yield of 97% and a purity of 97%.

Comparative Example 1

In this comparative example, the preparation of 2-methyl-4-amino-5-aminomethyl pyrimidine was performed in a batch reactor, which was specifically described as follows.

5 g of ammonia water (25% by weight) was mixed into 200 mL of methanol to which 2 g (0.015 mol) of 2-methyl-4-amino-5-cyanopyrimidine was added to obtain a substrate solution. The substrate solution and the modified Raney nickel catalyst prepared in Example 1 were added into the batch reactor. The batch reactor was vacuumized at a gauge pressure of 0.05 MPa for 10 min, and the gas in the batch reactor was replaced with nitrogen three times at 0.5 MPa and then replaced with hydrogen three times at 0.5 MPa. The batch reactor was subjected to leakage detection to confirm that the batch reactor was well sealed. A hydrogen gas inlet valve was opened to adjust a pressure in the batch reactor to 3 MPa. The reaction mixture was reacted at 100° C. under stirring at 900 r/min, and during the reaction, the reaction mixture was regularly sampled for analysis. The results demonstrated that the substrate 2-methyl-4-amino-5-cyanopyrimidine experienced a conversion of about 53% after 2 h; about 82% after 3 h; and about 99% after 5 h, and after 5 h, the product 2-methyl-4-amino-5-aminomethyl pyrimidine achieved a yield of 99% with purity of 96%.

The Comparative Example 1 and Example 1 had the same ratio of the 2-methyl-4-amino-5-cyanopyrimidine to the modified Raney nickel catalyst. Compared to the batch reactor, the micro-reaction system provided herein can greatly shorten the reaction time, significantly improve the yield of 2-methyl-4-amino-5-aminomethyl pyrimidine (>99%). Moreover, stirring device was not required in this micro-reaction system, which greatly reduced energy consumption. The method provided herein for preparing 2-methyl-4-amino-5-aminomethyl pyrimidine had advantages of continuous process, simple operation, high degree of automation, and greatly improved efficiency. Furthermore, the continuous flow synthesis method had a small online liquid holdup and the micro-channel reactor possessed excellent mass transfer and heat transfer characteristics, which rendered the process intrinsically safe, effectively reducing the safety risk in the catalytic hydrogenation in the batch reactor.

It should be noted that described above are merely preferred embodiments of the invention, which are not intended to limit the invention. It should be understood that any modification, change and replacement made by those skilled in the art without departing from the spirit of the invention should fall within the scope of the invention.

What is claimed is:

1. A method for preparing 2-methyl-4-amino-5-aminomethyl pyrimidine using a micro-reaction system, the micro-reaction system comprising a micro-mixer and a micro-channel reactor communicated in sequence; and the method comprising:
(1) modifying a Raney nickel catalyst with formalin to obtain a modified Raney nickel catalyst; and filling the micro-channel reactor with the modified Raney nickel catalyst;
(2) transporting a substrate solution containing 2-methyl-4-amino-5-cyanopyrimidine and a base and hydrogen to the micro-mixer followed by mixing; allowing the reaction mixture flowing out of the micro-mixer to enter the micro-channel reactor; and subjecting the reaction mixture to catalytic hydrogenation; and
(3) collecting the reaction mixture flowing out of the micro-reaction system; and subjecting the reaction mixture to separation and purification to obtain a target product 2-methyl-4-amino-5-aminomethyl pyrimidine;
wherein the 2-methyl-4-amino-5-aminomethyl pyrimidine is shown in formula (I), and the 2-methyl-4-amino-5-cyanopyrimidine is shown in formula (II); and the catalytic hydrogenation is shown in the following reaction scheme:

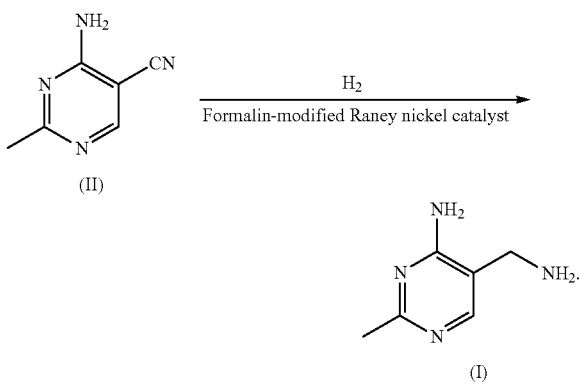

2. The method of claim 1, wherein the step (1) comprises:
(a) dispersing the Raney nickel catalyst in a liquid dispersion medium; adding a formalin solution, where the formalin solution is 0.5-30% by weight of the Raney nickel catalyst; and stirring the reaction mixture at 10-75° C. for 10 min-3 h in an inert gas; and
(b) filtering the reaction mixture to collect a filter residue; washing the filter residue with deionized water several times to obtain the modified Raney nickel catalyst; and storing the modified Raney nickel catalyst in water;
wherein a particle size of the Raney nickel catalyst is equal to or larger than 20 mesh;
a weight ratio of the Raney nickel catalyst to the liquid dispersion medium is (0.1-0.65):1;
the liquid dispersion medium is water, an organic solvent or a mixture thereof;
the organic solvent is a C1-C4 alkanol selected from the group consisting of methanol, ethanol, ethylene glycol, 1-propanol, 2-propanol, 1,2-propanediol, 1,3-propanediol, 1-butanol and a combination thereof;
the liquid dispersion medium is a mixture of water and one organic solvent, such as a mixture of water and methanol and a mixture of water and ethanol, or a mixture of two or more organic solvents, such as a mixture of ethanol and ethylene glycol; and
the inert gas is selected from the group consisting of nitrogen, argon, helium and neon.

3. The method of claim 1, wherein in step (2), the substrate solution is prepared by dissolving 2-methyl-4-amino-5-cyanopyrimidine and the base in methanol;
the base is an inorganic base or an organic base; wherein the inorganic base is ammonia water or hydrazine hydrate; and the organic base is selected from the group consisting of methylamine, urea, ethylamine, ethanolamine, ethylenediamine, dimethylamine, trimethylamine, triethylamine, propylamine, isopropylamine, 1,3-propanediamine, 1,2-propanediamine, tripropylamine, triethanolamine, butylamine, isobutylamine, tert-butylamine, tributylamine, hexylamine, octylamine, aniline, benzylamine, cyclohexylamine and pyridine.

4. The method of claim 3, wherein in the substrate solution, a molar ratio of 2-methyl-4-amino-5-cyanopyrimidine to the base is 1:(1-10).

5. The method of claim 1, wherein in step (2), a temperature in the micro-mixer is controlled to 5-120° C.; a temperature in the micro-channel reactor is controlled to 20-150° C.

6. The method of claim 1, wherein in step (2), flow rates of the substrate solution and hydrogen gas are adjusted such that a molar ratio of 2-methyl-4-amino-5-cyanopyrimidine to hydrogen gas in the micro-mixer is 1:(0.95-4); and a residence time of the reaction mixture in the micro-channel reactor is 0.1-15 min.

7. The method of claim 1, wherein the micro-mixer is a static mixer, a T-type micro-mixer, a Y-type micro-mixer, a coaxial flow micro-mixer or a flow-focusing micro-mixer.

8. The method of claim 1, wherein the micro-channel reactor is a tubular micro-channel reactor or a plate-type micro-channel reactor;
an inner diameter of the tubular micro-channel reactor is 100 μm-50 mm; or
a hydraulic diameter of a reaction fluid channel of the plate-type micro-channel reactor is 100 μm-50 mm.

9. The method of claim 1, wherein the micro-reaction system further comprises a feed pump, a gas mass flow meter equipped with a flow controller, a condenser, a gas-liquid separator, and a back pressure valve; one inlet of the micro-mixer is connected to the gas mass flow meter, and the other inlet of the micro-mixer is connected to the feed pump; an outlet of the micro-mixer is connected to an inlet of the micro-channel reactor, and an outlet of the micro-channel reactor is connected to an inlet of the condenser; a top of the gas-liquid separator is provided with a first port, a second port and a third port; an outlet of the condenser is connected to the first port; the second port is configured introduce nitrogen to provide a pressure in the gas-liquid separator; a pressure of the nitrogen is 0.1-4.5 MPa; the third port is connected to the back pressure valve; a back pressure of the back pressure valve is 0.1-4 MPa; and a pressure of the nitrogen is 0.2-0.5 MPa larger than a back pressure value set by the back pressure valve.

10. A micro-reaction system for preparing 2-methyl-4-amino-5-aminomethyl pyrimidine, comprising:
a feed pump;
a gas mass flow meter equipped with a flow controller;
a micro-mixer;
a micro-channel reactor;
a condenser;
a gas-liquid separator; and
a back pressure valve;

wherein the micro-mixer is provided with two inlets; one inlet of the micro-mixer is connected to the gas mass flow meter, and the other inlet of the micro-mixer is connected to the feed pump; an outlet of the micro-mixer is connected to an inlet of the micro-channel reactor, and an outlet of the micro-channel reactor is connected to an inlet of the condenser; a top of the gas-liquid separator is provided with a first port, a second port and a third port; an outlet of the condenser is connected to the first port; the second port is configured to introduce nitrogen to provide a pressure in the gas-liquid separator; a pressure of the nitrogen is 0.1-4.5 MPa; the back pressure valve is connected to the third port, and a back pressure of the back pressure valve is 0.1-4 MPa; and a pressure of the nitrogen is 0.2-0.5 MPa larger than a back pressure value set by the back pressure valve;

the micro-channel reactor is filled with a formalin-modified Raney nickel catalyst;

the feed pump and the gas mass flow meter are configured to transport a substrate solution containing 2-methyl-4-amino-5-cyanopyrimidine and hydrogen to the micro-mixer, respectively; the micro-mixer is configured for mixing the substrate solution with hydrogen obtain a reaction mixture; the reaction mixture flowing out of the micro-mixer enters into the micro-channel reactor and undergoes a catalytic hydrogenation; after flowing out of the micro-channel reactor, the reaction mixture is condensed in the condenser, and then enters the gas-liquid separator, a waste gas generated in the gas-liquid separator is discharged through the third port and the back pressure valve; and the reaction mixture is discharged through an outlet provided at a bottom of the gas-liquid separator, collected and subjected to separation and purification to obtain a target product 2-methyl-4-amino-5-aminomethyl pyrimidine;

wherein the 2-methyl-4-amino-5-aminomethyl pyrimidine is shown in formula (I):

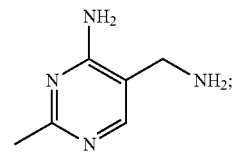

and the 2-methyl-4-amino-5-cyanopyrimidine is shown in formula (II):

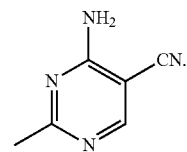

\* \* \* \* \*